United States Patent [19]
Hu et al.

[11] Patent Number: 5,495,107
[45] Date of Patent: Feb. 27, 1996

[54] ANALYSIS

[75] Inventors: Ke Hu, Franklin; Garry C. Kunselman, Stow; Carrol J. Hoffman, Westwood, all of Mass.

[73] Assignee: Thermo Jarrell Ash Corporation, Franklin, Mass.

[21] Appl. No.: 223,980

[22] Filed: Apr. 6, 1994

[51] Int. Cl.⁶ .................................................. G01N 21/17
[52] U.S. Cl. ........................ 150/281; 250/282; 356/316
[58] Field of Search .................................. 250/281, 282, 250/289; 356/72, 316

[56] References Cited

U.S. PATENT DOCUMENTS

| | | | |
|---|---|---|---|
| 3,616,596 | 11/1971 | Campargue | 55/17 |
| 3,937,954 | 2/1976 | Fite | 250/282 |
| 4,047,030 | 9/1977 | Lobach | 250/281 |
| 4,358,302 | 11/1982 | Dahneke | 55/392 |
| 4,682,026 | 7/1987 | Douglas | 250/288 |
| 4,740,696 | 4/1988 | Osawa et al. | 250/288 |
| 4,760,253 | 7/1988 | Hutton | 250/288 |
| 4,794,252 | 12/1988 | Bateman et al. | 250/288 |
| 4,812,040 | 3/1989 | Marcus et al. | 356/314 |
| 4,853,539 | 8/1989 | Hall et al. | 250/288 |
| 4,891,515 | 1/1990 | Jones et al. | 250/288 |
| 4,955,717 | 9/1990 | Henderson | 356/316 |
| 5,036,195 | 7/1991 | Batey et al. | 250/288 |
| 5,051,584 | 9/1991 | Gray et al. | 250/288 |
| 5,088,823 | 2/1992 | Smith, Jr. et al. | 356/328 |
| 5,130,537 | 7/1992 | Okamoto et al. | 250/281 |
| 5,148,021 | 9/1992 | Okamoto et al. | 250/288 |
| 5,185,523 | 2/1993 | Kitagawa et al. | 250/281 |
| 5,202,562 | 4/1993 | Koga et al. | 250/281 |
| 5,252,827 | 10/1993 | Koga et al. | 250/281 |
| 5,383,019 | 1/1995 | Farrell et al. | 250/288 |

FOREIGN PATENT DOCUMENTS

| | | | |
|---|---|---|---|
| 515352 | 11/1992 | European Pat. Off. | 250/281 |
| 62-26757 | 2/1987 | Japan . | |
| 1242031 | 8/1971 | United Kingdom . | |
| 1460634 | 1/1977 | United Kingdom . | |
| 1515406 | 6/1978 | United Kingdom . | |
| 2176649 | 12/1986 | United Kingdom . | |
| 2219432 | 12/1989 | United Kingdom . | |
| 2267994 | 12/1993 | United Kingdom . | |

OTHER PUBLICATIONS

Houk, "Mass Spectrometry of Inductively Coupled Plasmas," *Analytical Chemistry*, vol. 58, No. 1, Jan. 1986, pp. 97–105.

Garbarino, et al., "Simultaneous Determination of Major And Trace Elements By Inductively Coupled Plasma Mass Spectrometry/Optical Emission Spectrometry," Anal. Chem. 61:793–796 (1989).

R. Champargue, "Progress In Overexpanded Supersonic Jets And Skimmed Molecular Beams In Free–Jet Zones Of Silence," J. Phys. Chem. 88:4466–4474 (1984).

(List continued on next page.)

*American Society For Mass Spectrometry*, 1993, pp. 28–37.

*Primary Examiner*—Jack I. Berman
*Assistant Examiner*—Kiet T. Nguyen
*Attorney, Agent, or Firm*—Fish & Richardson

[57] ABSTRACT

An analysis system includes induction coupled plasma apparatus into which sample material to be analyzed is introduced for excitation in the plasma, optical measuring apparatus coupled to the induction coupled plasma apparatus for analyzing the sample material, and mass spectrometer apparatus also coupled to the induction coupled plasma apparatus for analyzing the sample material. The mass spectrometer apparatus includes structure defining a first region, a sampling member adjacent the induction coupled plasma apparatus that has an orifice through which at least some ions characteristic of the sample material may pass into the first region, structure defining a second region, and a gate valve between the first and second regions. The gate valve is open when the analysis system is operating in mass spectrometer mode, and is closed when the system is operating only in optical measuring mode. Inert gas is flowed outwardly through the sampling member orifice towards the induction coupled plasma apparatus from the first region of the mass spectrometer when the analysis system is operating in the optical measuring mode.

29 Claims, 7 Drawing Sheets

OTHER PUBLICATIONS

Olivares, "Continuum Flow Sampling Mass Spectrometer For Elemental Analysis With An Inductively Coupled Plasma Ion Source", Jun., 1985.

Randall, et al., "Direct Coupling Of A Dense (supercritical) Gas Chromatograph To A Mass Spectrometer Using A Supersonic Molecular Beam Interface," Rev. Sci Instrum. 52(9):1283–1295 Sep. 1981.

Gentry, "High–Percision Skimmers For Supersonic Molecular Beams," Rev. Sci. Instrum. 46(1):104 Jan. 1925.

Turner, "Some Observations on Mass Bias Effects Occurring in ICP–MS Systems", *Application of Plasma Source Mass Spectrometry*, pp. 71–78 (1991).

Hu, K et al. "Inductively Coupled Plasma Mass Spectrometry With an Enlarged Sampling Orifice and Offset Ion Lens. I. Ion Trajectories and Detector Performance", *American Society For Mass Spectrometry*, 1993, pp. 16–27.

Hu, K et al. "Inductively Coupled Plasma Mass Spectrometry With An Enlarged Sampling Orifice and Offset Ion Lens. II. Polyatomic Ion interferences and Matrix Effects",

ANALYSIS

FIELD OF THE INVENTION

This invention relates to analytical processes and systems, and more particularly to analytical processes and systems which are able to operate over a wide dynamic range of concentrations.

BACKGROUND OF THE INVENTION

Induction coupled plasma devices have been employed for generating a high temperature plasma into which a sample solution to be analyzed is introduced for dissociation, atomization and ionization. The resulting material may be analyzed using a mass spectrometer or an optical measuring apparatus such as an atomic absorption spectrophotometer or an emission spectrophotometer. Detection limit values of optical measuring apparatus are in the sub-PPB level while detection limit values of mass spectrometers may be in the PPT level.

SUMMARY OF THE INVENTION

In accordance with one aspect of the invention, there is provided an analysis system that includes induction coupled plasma apparatus into which a solution of sample material to be analyzed is introduced for excitation in the plasma, optical measuring apparatus coupled to the induction coupled plasma apparatus for analyzing elements of the sample, and mass spectrometer apparatus also coupled to the induction coupled plasma apparatus for analyzing the sample material. The mass spectrometer apparatus includes structure defining a first region, a sampling member adjacent the induction coupled plasma apparatus that has an orifice through which at least some ions characteristic of the sample material may pass into the first region, structure defining a second region, pump structure coupled to the second region for reducing the pressure in the second region below the pressure in the first region, valve structure disposed between the induction coupled plasma apparatus and the second region, operator apparatus coupled to the valve structure for maintaining the valve open when the analysis system is operating in mass spectrometer mode, and maintaining the valve closed when the system is operating only in optical measuring mode. Preferably, the system includes structure for flowing an inert gas outwardly through the orifice towards the induction coupled plasma apparatus from the first region when the analysis system is operating in the optical measuring mode.

Preferably, ion lens structure is disposed in the first region immediately adjacent the valve structure, and a voltage in the range of −750 to −1,500 volts is applied to that ion lens structure; and the mass spectrometer includes a mass spectrometric separating system, ion detector apparatus, and focusing apparatus disposed between the source and the separating system, the focusing apparatus comprising an asymmetric electrostatic focusing lens system with a lens axis, an ion entrance aperture, an ion exit aperture and intermediate electrode structure disposed between the entrance and exit apertures having an aperture offset from the lens axis, and circuitry for applying a deflecting voltage to the intermediate electrode structure.

In a particular embodiment, the optical analysis apparatus includes a solid state detector with a two dimensional detector pixel array; and the system includes diluter structure for diluting the sample material introduced into the induction coupled plasma apparatus to a dissolved solids content of less than 0.2 percent.

In accordance with another aspect of the invention, there is provided a mass spectrometer with ion source structure for generating ions of a sample material to be analyzed, structure defining first and second regions adapted to be evacuated, sampling structure adjacent the ion source structure having an orifice through which at least some ions characteristic of the sample material may pass into the first region, focusing apparatus disposed in the first region, mass spectrometric separating apparatus disposed in the second region, ion detector apparatus coupled to the separating apparatus, and differential pumping structure between the first and second regions, the differential pumping structure having a tubular passage of at least five millimeters length and that extends into the second region with an exit port in overlapping relation to the separating apparatus so that ions are shielded from separating apparatus fringe magnetic fields and the stability of the magnetic field of the separating apparatus, particularly with respect to low mass (below 40) elements, is improved.

Preferably, the mass spectrometer separating apparatus includes a plurality of mass separation rods (that in a particular embodiment are quadrapole rods) and the exit port of the differential pumping structure is disposed within the entrance ends of the mass separation rods. The focusing apparatus comprises an asymmetric electrostatic focusing lens system disposed in front of the differential pumping structure with a lens axis, a conical electrode member that defines an ion entrance aperture, a planar electrode member that defines an ion exit aperture and an intermediate planar electrode member disposed between the entrance and exit apertures that has an aperture offset from the lens axis, and circuitry for applying deflecting voltages to the electrode members. In a particular embodiment, the circuitry applies a voltage in the range of −750 to −1500 volts to the conical leading ion lens electrode member.

In accordance with another aspect of the invention, there is provided a mass spectrometer with ion source structure for generating ions of a sample material to be analyzed, structure defining first and second regions adapted to be evacuated, sampling structure adjacent the ion source structure having an orifice through which at least some ions characteristic of said sample material may pass into the first region, focusing apparatus disposed in the first region, mass spectrometric separating apparatus disposed in the second region, ion detector apparatus coupled to the separating apparatus, and exit lens structure between the separating apparatus and the detector apparatus. The exit lens structure has an entrance port of at least one centimeter diameter, an exit port of less than half the diameter of the entrance port, and passage structure that connects the entrance and exit ports, the passage structure having a length of at least five millimeters and being smoothly tapered for reducing background noise due to unwanted neutrals and photons.

In accordance with still another aspect of the invention, there is provided a mass spectrometer with an entrance axis, ion source structure for generating ions of a sample material to be analyzed for passage along the entrance axis, structure defining first and second regions adapted to be evacuated, sampler cone structure, skimmer cone structure, collection lens cone structure, focusing apparatus disposed in the first region, the focusing apparatus including ion lens cone structure. Each of the cone structures has an orifice and the orifices are disposed in series along the entrance axis. Mass spectrometric separating apparatus is disposed in the second region, and ion detector apparatus is coupled to the separating apparatus. While it will be understood that other ion sources may De used as appropriate in other embodiments in a particular embodiment, the ion source structure is inductively coupled plasma apparatus and an optically measuring spectrometer is coupled optically to the plasma apparatus. Valve structure is disposed between the collection lens cone structure and the ion lens cone structure. Operator apparatus is coupled to the valve structure and maintains the valve open when the analysis system is operating in mass spectrometer mode, and maintains the valve closed when the system is operating in only optical measuring mode. Structure flows an inert gas outwardly through the sampler and skimmer cone orifices towards the induction coupled plasma apparatus when the analysis system is operating only in the optical measuring mode. The optical analysis spectrometer includes a solid state detector with a two dimensional detector pixel array; and the system includes diluter structure for diluting the sample material introduced into the induction coupled plasma apparatus to a dissolved solids content of less than 0.2 percent for minimizing salt build-up on surfaces or the sampler and skimmer cone structures.

In accordance with another aspect of the invention, there is provided an analysis process that includes the steps of providing induction coupled plasma apparatus optical analysis apparatus optically coupled to the induction coupled plasma apparatus for analyzing the sample material, mass spectrometer apparatus coupled to the induction coupled plasma apparatus for analyzing the sample material, diluter apparatus and controller structure introducing sample material to be analyzed into the Induction coupled plasma apparatus, operating the diluter apparatus to dilute the sample material introduced into the induction coupled plasma apparatus to a solids content of less than 0.2 percent; and sensing outputs from the induction coupled plasma apparatus and the optical analysis apparatus and the mass spectrometer apparatus to analyze the sample material.

Preferably, the mass spectrometer apparatus includes structure defining a first region, a sampling member adjacent the induction coupled plasma apparatus that has an orifice through which at least some ions characteristic of the sample material may pass into the first region, structure defining a second region, pump structure coupled to the second region for reducing the pressure in the second region on below the pressure in the first region, and valve structure disposed between the induction coupled plasma apparatus and the second region, and the process further including the steps of maintaining the valve structure in open position when the analysis process is operating in mass spectrometer mode and maintaining the valve structure in closed position when the process is operating only in optical analysis mode; and the step of flowing an inert gas from the first region outwardly through the orifice towards the induction coupled plasma apparatus when the valve structure is in closed position.

The system and process provides versatility and flexibility, the mass spectrometer has excellent detection limits, improved sensitivity, low background and low interferences, and the optical analysis spectrometer extends the analysis range of the system and process.

BRIEF DESCRIPTION OF THE DRAWINGS

Other features and advantages of the invention will be seen as the following description of a particular embodiment progresses, in conjunction with the drawings, in which.

DESCRIPTION OF PARTICULAR EMBODIMENT

Figure 1:
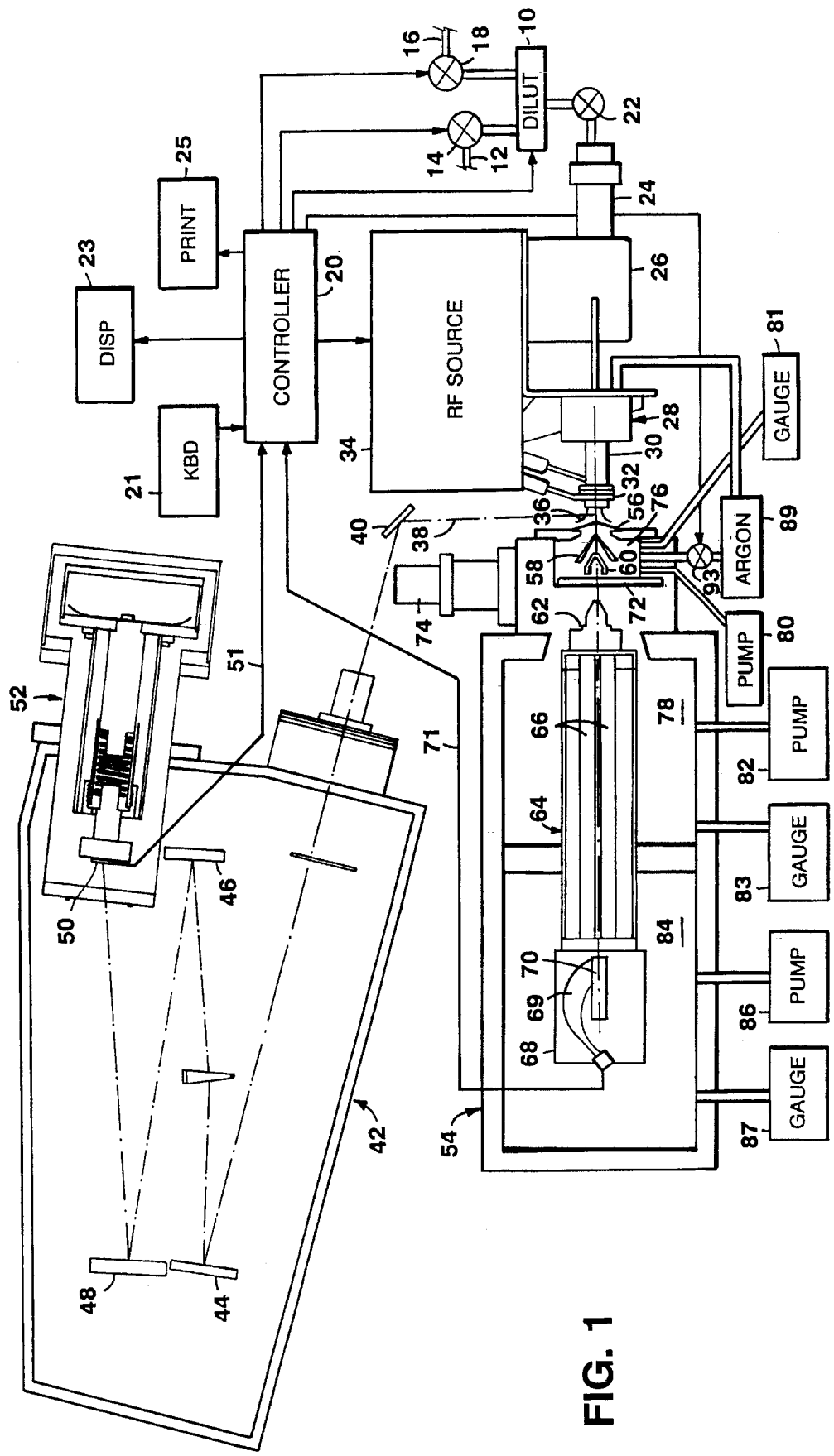
FIG. 1 is a diagrammatic view of an analysis system in accordance with the invention.
Figure 3:
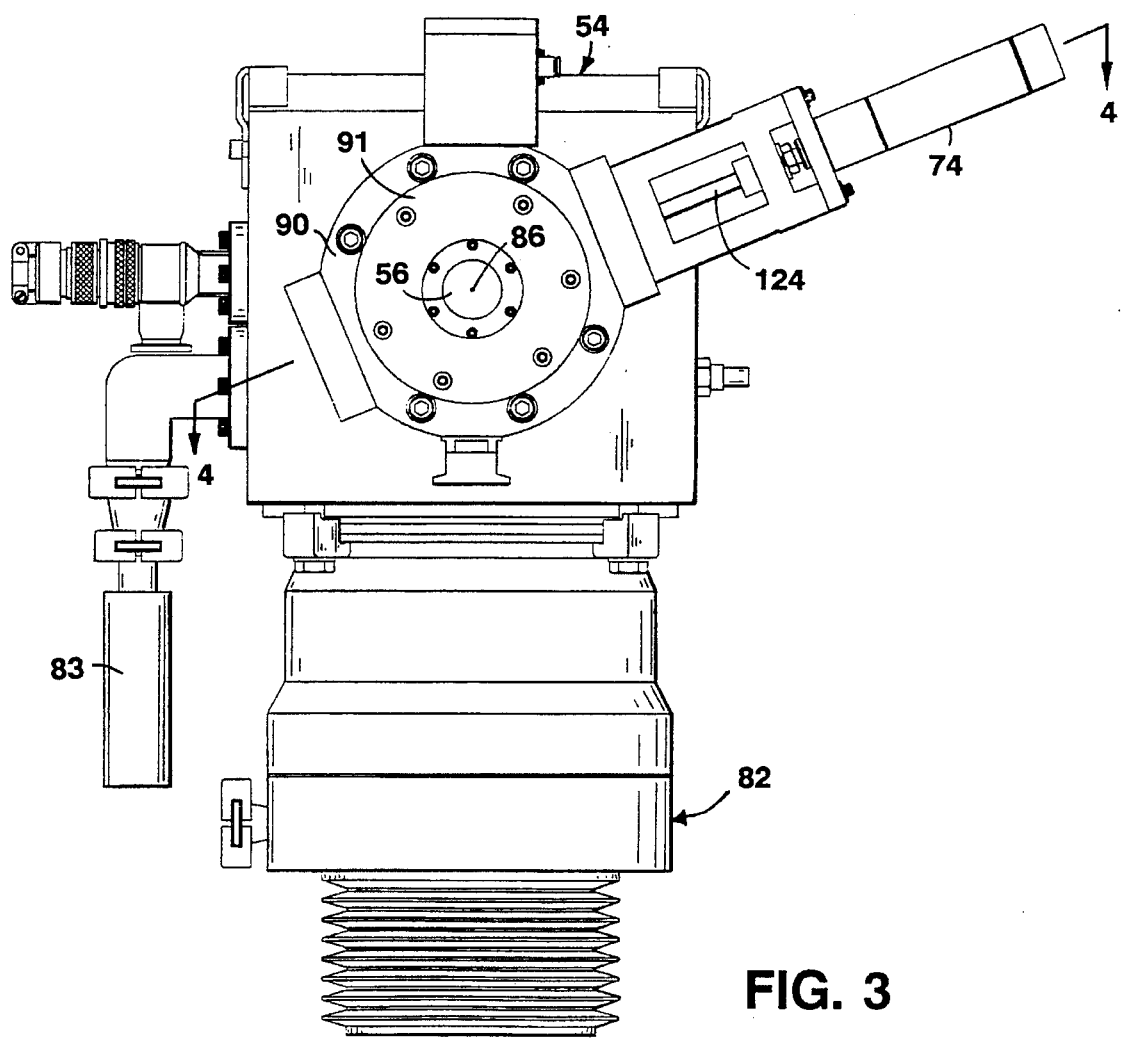
FIG. 3 is an end view of the mass spectrometer apparatus shown in FIG. 2.
Figure 2:
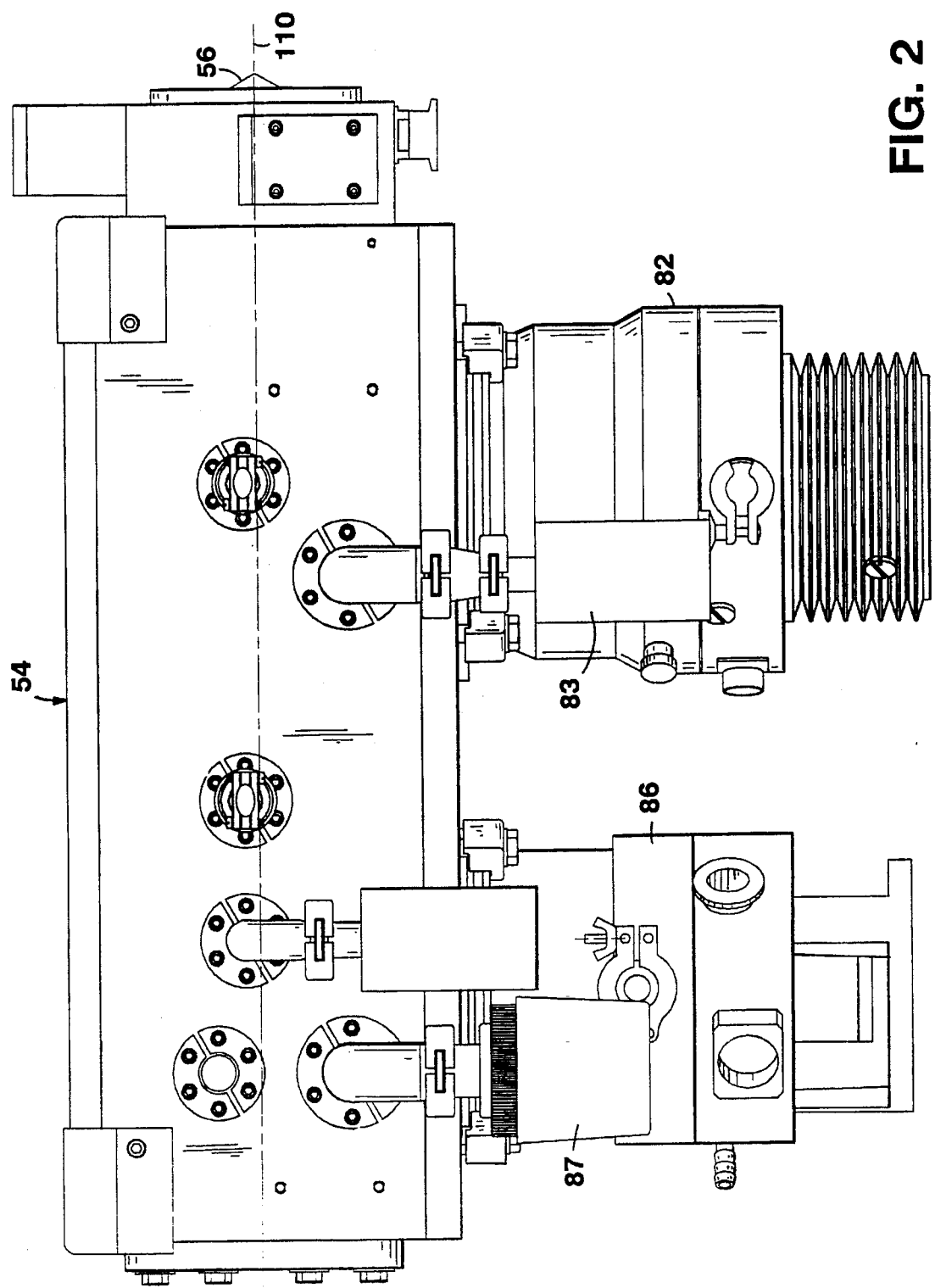
FIG. 2 is a side view of mass spectrometer apparatus employed in the system of FIG. 1.

The analysis system shown in FIG. 1 includes diluter 10, with sample inlet 12 through piston pump 14, and deionized water inlet 16 through piston pump 18. Pumps 14, are connected to controller 20 and the output of diluter is connected through peristaltic pump 22 to cross flow nebulizer 24 and spray chamber 26 that is connected to plasma torch assembly 28 for introducing sample material solutions to be analyzed into tube 30 of torch assembly 28. Coupled to controller 20 are input keyboard 21, display 23 and printer 25. Surrounding tube 30 is induction coil 32 that is coupled to two kilowatt crystal controlled 27.12 megahertz RF generator 34. The sample material is excited to spectroemissive levels in plasma 36 and a beam 38 of radiation from plasma 36 is reflected by mirror 40 into echelle spectrograph 42 for reflection by collimating mirror 44 and dispersion by echelle grating 46 and reflection by mirror 48 for sensing by solid state (CID) detector 50 that includes an array of 388×244 detector pixels, and that is coupled to dewar 52 for cooling detector 50, and that provides an output over line 51 to controller 20. Spectrograph 42 operates over a wavelength range of 190–900 nanometers, and is of the type shown in Smith U.S. Pat. No. 5,088,823, the disclosure of which is expressly incorporated herein by reference.

Also coupled to the output plasma 36 is mass spectrometer 54 whose structure is shown in more detail in FIGS. 2–8. Mass spectrometer 54 includes sampling cone 56, skimmer cone 58, collection lens 60, ion lens assembly 62, quadrapole mass analyzer 64 that includes four hyperbolic Invar rods 66; and detector system 68 that includes electron multiplier 69 and deflector 70 and that is coupled over line 71 to controller 20. Gate valve 72 is disposed between collection lens element 60 and ion lens assembly 62 (between expansion chamber 76 and ion lens chamber 78) and is operated by pneumatic cylinder 74.

When the analysis system of FIG. 1 is operating in mass spectrometer mode, gate valve 72 is open and ions characteristic of the sample material and present in plasma 36 enter mass spectrometer 54 through orifice 86 (FIG. 4) of sampling cone 56. Expansion chamber 76 is pumped by rotary pump 80 at a pumping speed of about ten liters per second to provide a pressure of about three torr in chamber 76 as monitored by thermo-couple gage 81; ion lens chamber 78 is pumped by turbo pump 82 at a pumping speed of 500 liters per second to maintain a pressure of about $3 \times 10^{-4}$ torr in chamber 78 as monitored by pirani gauge 83; and quadrapole and detector chamber 84 is pumped by turbomolecular pump 86 at a pumping speed of 400 liters per second to maintain a pressure of about 2×10⁻⁶ torr in chamber 84 as monitored by magnetron gage 87.

When the analysis system is operating in emission spectrograph mode, gate valve 72 is closed and argon from argon source 89 (as controlled by controller 20 and valve 93) is flowed from expansion chamber 76 out through orifices 88, 86 (FIG. 4) of skimmer cone 58 and sampling cone 56 at a rate of about one liter per minute to minimize salt buildup on surfaces of cones 56, 58. One or more major elements such as sodium, potassium, calcium or iron are monitored and controller 20 operates diluter 10 to control the dilution of the sample to a dissolved solids content of the sample less than 0.2 percent. The system can also be run in emission and mass spectrometer modes simultaneously (as with samples of known low dissolved solids content such as rain water or a pure acid) but the orifice protection feature is not used during such simultaneous operation as gate valve 72 is open.

Figure 4:
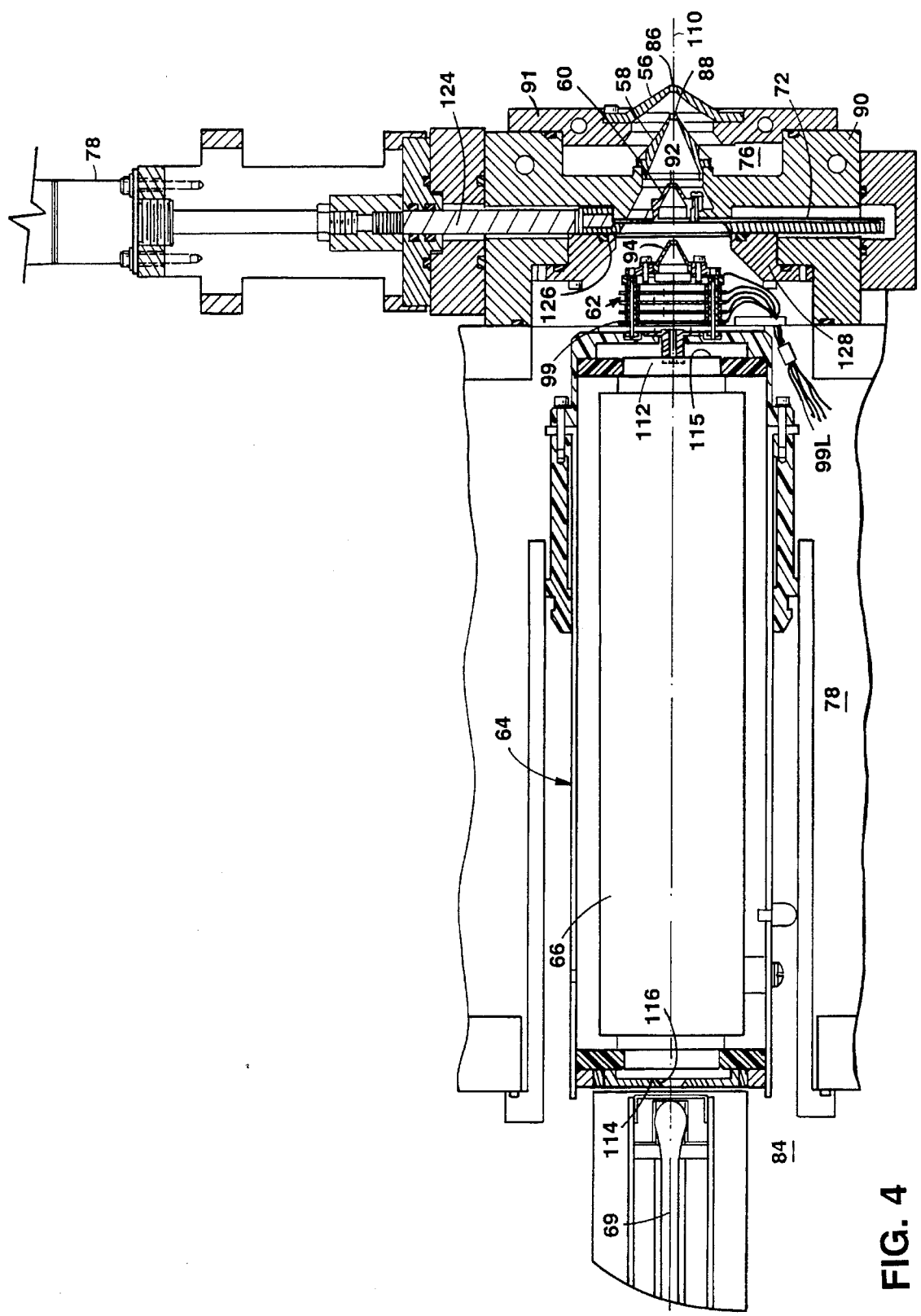
FIG. 4 is a sectional view taken along the line 4—4 of FIG. 3.

With reference to FIG. 4, sampling cone 56, skimmer cone 58, collection lens 60 and the first ion lens electrode 94 are conical members of nickel and are disposed in sequence with their orifices on the entrance axis 110 of mass spectrometer 54. The diameter of sampler cone orifice 86 is 1.2 millimeter and the diameter of skimmer cone orifice 88 is one millimeter. The distance between orifices 86, 88 is about eight millimeters. Sampling cone 56 is mounted on water cooled copper face plate 91, and skimmer cone 56 is mounted on water cooled copper flange 90. Collection lens 60 has orifice 92 of about 1.2 millimeters, the next ion lens electrode 94 has orifice 104 of three millimeters diameter and the distance between collection lens 60 and the conical next ion lens electrode 94 is about eight millimeters. Gate valve 72 is disposed between cones 60 and 94. Ion lens electrodes 95–99 (see also FIG. 8) are ½ millimeter thick stainless steel plates that are separated by spacer insulators and to which separate voltages are applied over lines 95L–99L. Each collection lens plate 95–99 has an orifice 105–109 of about six millimeters diameter with orifices 105 and 106 on axis 110, orifices 107 and 109 being offset about three millimeters from axis 110, and orifice 108 being offset about seven millimeters from axis 110.

Between the ion lens assembly 62 and the quadrapole chamber 64 is differential pumping orifice member 112 that defines a cylindrical passage 111 that is about eight millimeters long and about three millimeters diameter with its exit port 113 disposed within and overlapping the entrance ends 115 of quadrupole rods 66 to shield ions exiting from passage 111 from quadrupole fringe magnetic fields and to improve the stability of the quadrupole magnetic field, particularly with respect to low mass (below 40) elements. Disposed in quadrupole chamber 64 are four, 250 millimeter long hyperbolic Invar rods 66 that define an $R_o$ of twelve millimeters. Ions leaving the quadrupole chamber 64 are focused through eight millimeter thick aluminum exit lens 114 (FIG. 4) that has conically-tapered through passage 116 that has an entrance diameter of thirteen millimeters and an exit diameter of five millimeters and are detected by a Channeltron Model 4870 electron multiplier 69. For maximizing transmission of $^{115}In^+$, the voltage applied to collection lens 60 was −1,000 volts; to ion lens 94 was −100 volts; to ion lens 95 was −25 volts; to ion lens 96 was +30 volts; to ion lens 97 was −150 volts; to ion lens 98 was +30 volts; to ion lens 99 was −50 volts; to exit lens 114 was −115 volts; deflector 70 has a deflection voltage of +10 volts applied to it; and electron multiplier 69 has a voltage more positive than −2500 volts applied to it when operating in analog mode and a voltage more negative than −3000 volts when operating in pulse counting mode.

Figure 5:
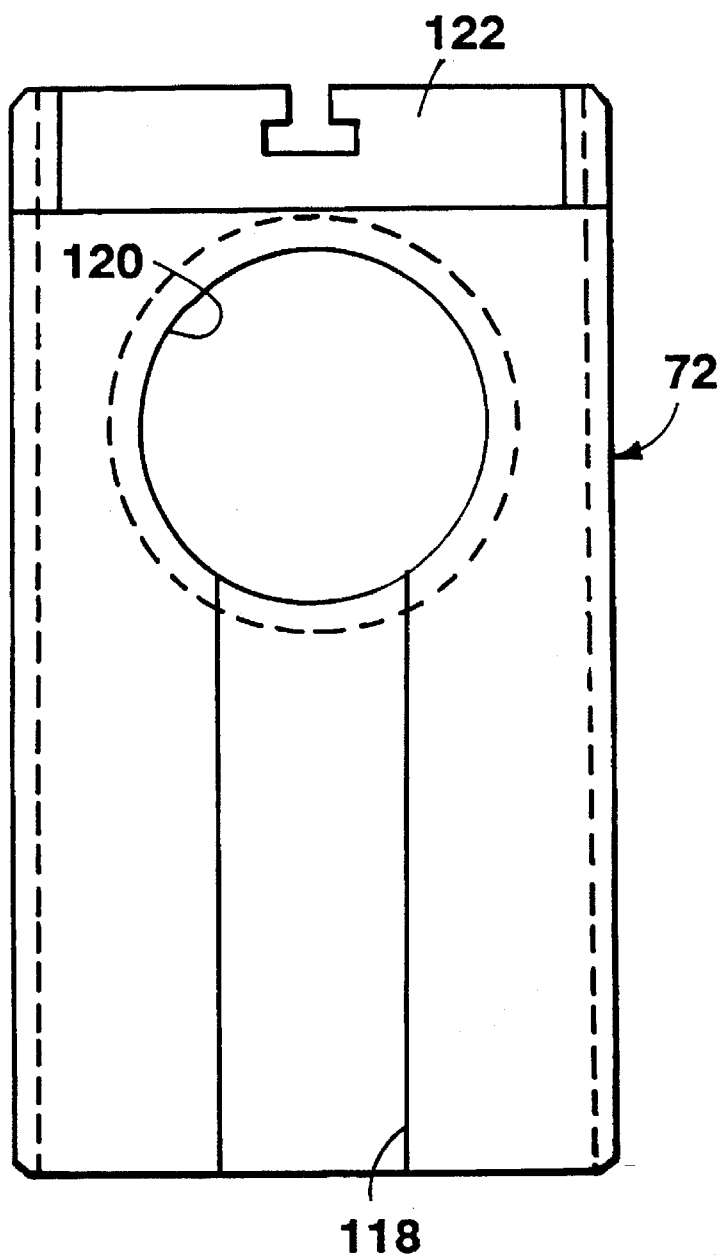
FIG. 5 is a front elevational view of a gate valve member employed in the mass spectrometer shown in FIG. 4.
Figure 6:
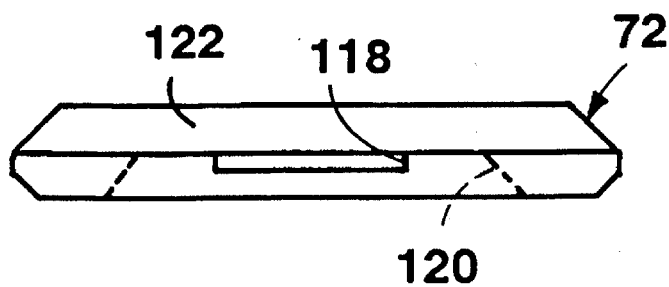
FIG. 6 is an end view of the gate valve member shown in FIG. 5.
Figure 7:
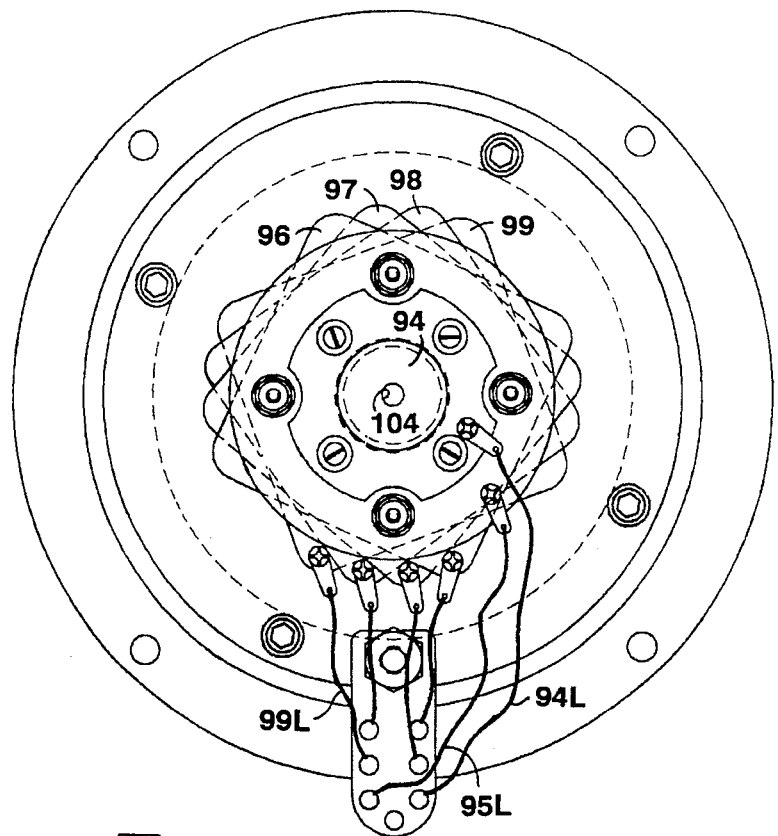
FIG. 7 is a front view of the ion lens assembly employed in the embodiment shown in FIG. 4.
Figure 8:
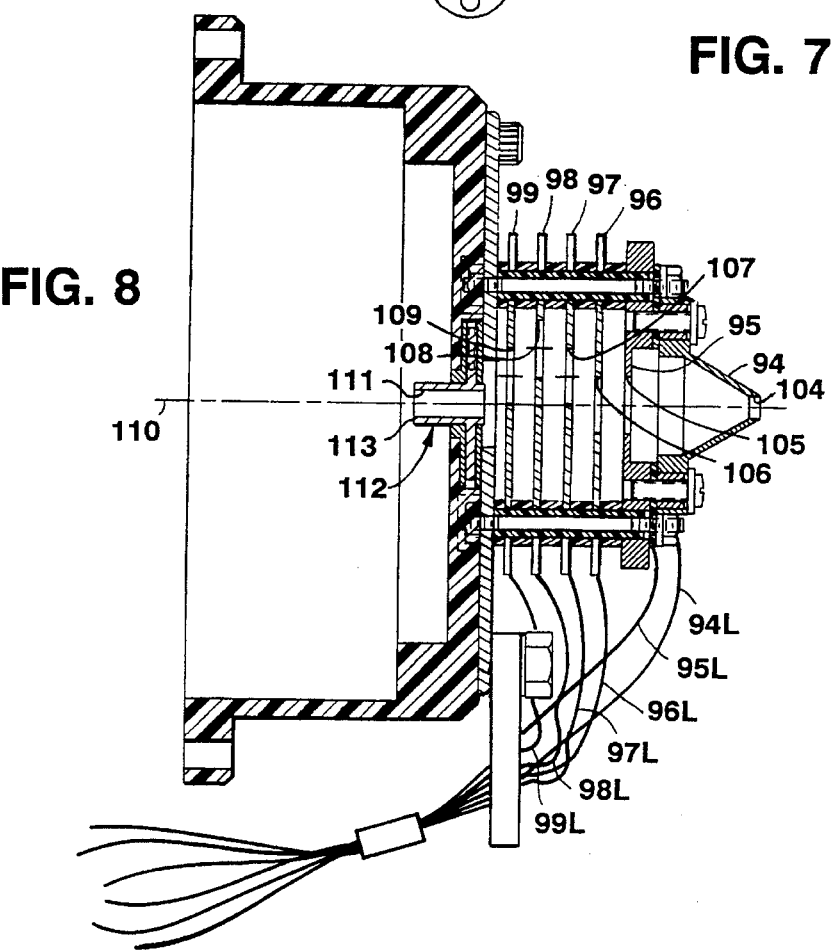
FIG. 8 is a sectional view taken along the line 8—8 of FIG. 7.

With reference to FIGS. 5 and 6, gate valve 72 is a stainless steel plate about six centimeters wide, about eleven centimeters long, and about 0.4 centimeter thick. Recess 118 extends from port 120 and has a width of about two centimeters and a depth of one millimeter. Port 120 has a diameter of about 3.5 centimeters. Coupling structure 122 connects gate valve 72 to actuator 74 through connecting rod 124. Seal ring 126 is seated in clamp ring 128 and provides a seal when the pressure in ion lens chamber 78 is less than the pressure in expansion chamber 76. As indicated above, when the analysis system is operating only in optical emission mode, gate valve 72 (port 120) is closed and maintained in a closed position and argon from source 89 is flowed from expansion chamber 76 through orifices 88, 86 at a rate of about one liter per minute to reduce orifice contamination. When the gate valve 72 is to be moved, the pressure in chamber 76 is decreased to about three torr, allowing freer movement of the gate valve 72.

Figure 9A:
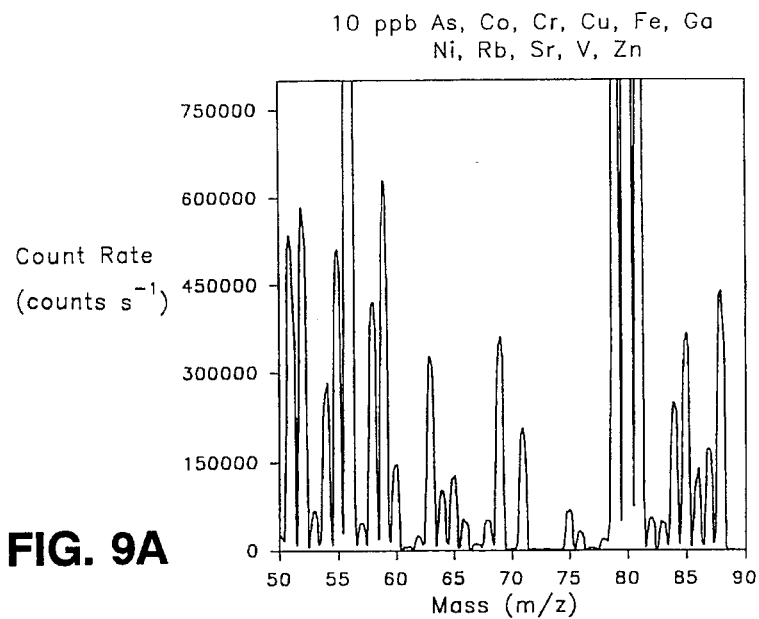
FIGS. 9a –9c are diagrams indicating mass spectra obtained with the system shown in FIG. 1.
Figure 9B:
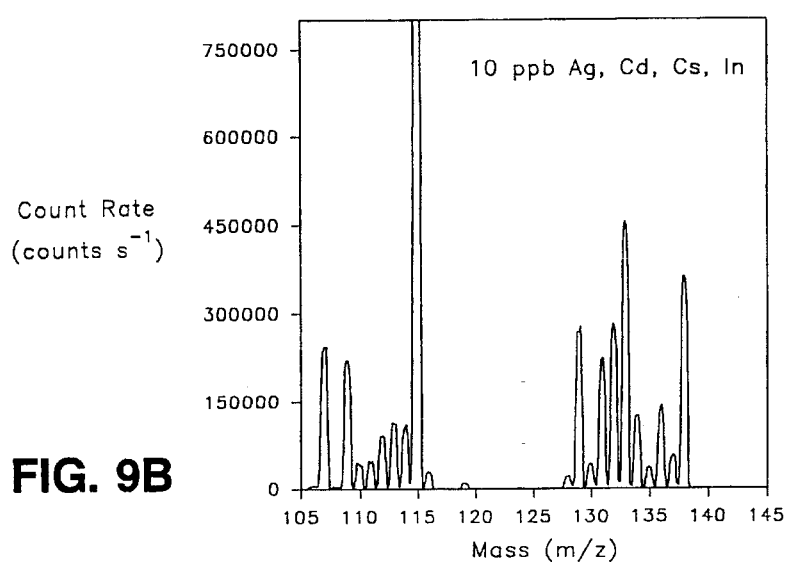
Figure 9C:
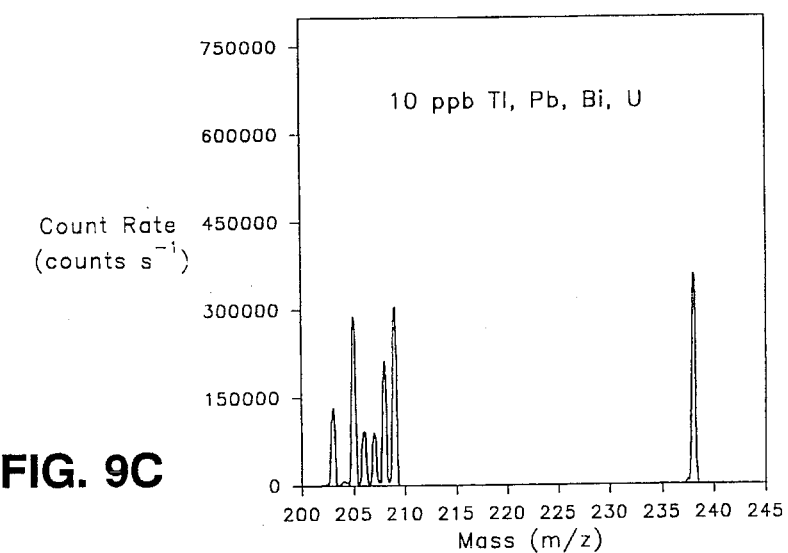

Mass spectra (plots of counts versus mass-to-charge ratio) obtained with the system in mass spectrometer mode (gate valve 72 open), of 10 ppb As, Co, Cr, Cu, Fe, Ga, Ni, Rb, Se, Sr, V and Zn ions are shown in FIG. 9a; mass spectra of 10 ppb Ag, Cd, Cs, and In ions are shown in FIG. 9b; and mass spectra of 10 ppb Bi, Pb, Tl, and U ions are shown in FIG. 9c.

The sensitivities and detection limits obtained with this mass spectrometer are listed in the following Table:

| Element | Sensitivity (counts s⁻¹/mg L⁻¹) | Detection Limits (ng L⁻¹) |
| --- | --- | --- |
| $^7Li$ | $3.20 \times 10^7$ | 2 |
| $^{59}Co$ | $6.71 \times 10^7$ | 1 |
| $^{89}Y$ | $6.47 \times 10^7$ | 0.7 |
| $^{109}Ag$ | $3.01 \times 10^7$ | 1 |
| $^{133}Cs$ | $5.20 \times 10^7$ | 1 |
| $^{159}Tb$ | $6.23 \times 10^7$ | 0.4 |
| $^{208}Pb$ | $2.68 \times 10^7$ | 1 |
| $^{209}Bi$ | $5.43 \times 10^7$ | 0.5 |
| $^{238}U$ | $6.13 \times 10^7$ | 0.3 |

While a particular embodiment of the invention has been shown and described, various modifications will be apparent to those of ordinary skill in the art, and therefore, it is not intended that the invention be limited to the disclosed embodiment, or to details thereof, and departures may be made therefrom within the spirit and scope of the invention.

What is claimed is:

1. An analysis system comprising:

induction coupled plasma apparatus, structure for introducing sample material to be analyzed into said induction coupled plasma apparatus, optical analysis apparatus optically coupled to said induction coupled plasma apparatus for analyzing said sample material, and mass spectrometer apparatus coupled to said induction coupled plasma apparatus for analyzing said sample material, said mass spectrometer apparatus including structure defining a first region, a sampling member adjacent said induction coupled plasma apparatus and having an orifice through which at least some ions characteristic of said sample material may pass into said first region, structure defining a second region, pump structure coupled to said second region for reducing the pressure in said second region below the pressure in said first region, valve structure disposed between said induction coupled plasma apparatus and said second region, and operator apparatus coupled to said valve structure for maintaining said valve structure in open position when said analysis system is operating in mass spectrometer mode and for maintaining said valve structure in closed position when said system is operating only in optical analysis apparatus mode.

2. The system of claim 1 wherein said valve structure includes gate valve structure disposed between said first and second regions.

3. The system of claim 2 and further including ion lens structure disposed in said first region immediately adjacent said gate valve structure, and circuitry for applying a voltage in the range of about −750 to −1,500 volts to said ion lens structure.

4. The system of claim 1 wherein said mass spectrometer apparatus includes a mass spectrometric separating apparatus, ion detector apparatus, and focusing apparatus disposed between said induction coupled plasma apparatus and said separating apparatus, said focusing apparatus comprising an asymmetric electrostatic focusing lens system with a lens axis, an ion entrance aperture, an ion exit aperture and intermediate electrode structure disposed between said entrance and exit apertures having an aperture offset from said lens axis, and circuitry for applying a deflecting voltage to said intermediate electrode structure.

5. The system of claim 4 and further including mass spectrometer differential pumping structure between said first and second regions, said differential pumping structure having a tubular passage and said passage extending into said second region with an exit port in overlapping relation to said separating apparatus.

6. The system of claim 5 wherein said separating apparatus includes a plurality of mass separating rods and said exit port of said differential pumping structure is disposed within the entrance ends of said mass separating rods.

7. The system of claim 4 and further including differential pumping structure between said first and second regions, said differential pumping structure having a tubular passage of at least five millimeters length and said passage extending into said second region with an exit port in overlapping relation to said separating apparatus.

8. The system of claim 7 wherein said separating apparatus includes a plurality of mass separating rods and said exit port of said differential pumping structure is disposed within the entrance ends of said mass separating rods.

9. The system of claim 1 wherein said mass spectrometer apparatus has an entrance axis and further including sample cone structure, skimmer cone structure, collection lens cone structure and ion lens cone structure, each said cone structure having an orifice and said orifices being disposed on said entrance axis.

10. The system of claim 1 wherein said optical analysis apparatus includes a solid state detector with a two dimensional detector pixel array.

11. The system of claim 1 and further including diluter apparatus and controller structure for operating said diluter apparatus to dilute the sample material introduced into said induction coupled plasma apparatus to a solids content of less than 0.2 percent.

12. An analysis system comprising:
induction coupled plasma apparatus, structure for introducing sample material to be analyzed into said induction coupled plasma apparatus, optical analysis apparatus optically coupled to said induction coupled plasma apparatus for analyzing said sample material, mass spectrometer apparatus coupled to said induction coupled plasma apparatus for analyzing said sample material, said mass spectrometer apparatus including structure defining a first region, sampling member adjacent said induction coupled plasma apparatus and having an orifice through which at least some ions characteristic of said sample material may pass into said first region structure defining a second region, pump structure coupled to said second region for reducing the pressure in said second region pressure in said first region, valve structure disposed between said induction coupled plasma apparatus and said second region, operator apparatus coupled to said valve structure for maintaining said valve structure in open position when said analysis system is operating in mass spectrometer mode and for maintaining said valve structure in closed position when said system is operating only in optical analysis apparatus mode, and structure for flowing an inert gas outwardly from said first region through said orifice towards said induction coupled plasma apparatus when said valve structure is closed.

13. An analysis system comprising:
induction coupled plasma apparatus, structure for introducing sample material to be analyzed into said induction coupled plasma apparatus, optical analysis apparatus optically coupled to said induction coupled plasma apparatus for analyzing said sample material, and mass spectrometer apparatus coupled to said induction coupled plasma apparatus for analyzing said sample material, said mass spectrometer apparatus having an entrance axis and further including mass spectrometric separating apparatus, ion detector apparatus, structure defining a first region, a sampling member adjacent said induction coupled plasma apparatus and having an orifice through which at least some ions characteristic of said sample material may pass into said first region, sample cone structure, skimmer cone structure, collection lens cone structure and ion lens cone structure, each said cone structure having an orifice and said orifices being disposed on said entrance axis, structure defining a second region, differential pumping structure between said first and second regions, said differential pumping structure having a tubular passage of at least five millimeters length and said passage extending into said second region with an exit port in overlapping relation to said separating apparatus, pump structure coupled to said second region for reducing the pressure in said second region below the pressure in said first region, valve structure disposed between said induction coupled plasma apparatus and said second region, operator apparatus coupled to said valve structure for maintaining said valve structure in open position when said analysis system is operating in mass spectrometer mode and for maintaining said valve structure in closed position when said system is operating only in optical analysis apparatus mode, said separating apparatus includes a plurality of mass separating rods and said exit port of said differential pumping structure being disposed within the entrance ends of said mass separating rods, and exit lens structure between said separating apparatus and said detector apparatus, said exit lens structure having an entrance port of at least one centimeter diameter, an exit port of less than half the diameter of said entrance port, and passage structure connecting said entrance and exit ports, said passage structure having a length of at least five millimeters and being smoothly tapered for reducing background noise due to unwanted neutrals and photons.

14. An analysis system comprising:
induction coupled plasma apparatus, structure for introducing sample material to be analyzed into said induction coupled plasma apparatus, optical analysis apparatus optically coupled to said induction coupled plasma apparatus for analyzing said sample material, mass spectrometer apparatus coupled to said induction coupled plasma apparatus for analyzing said sample material, said mass spectrometer apparatus including structure defining a first region, a sampling member adjacent said induction coupled plasma apparatus and having an orifice through which at least some ions characteristic of said sample material may pass into said first region, structure defining a second region, pump structure coupled to said second region for reducing the pressure in said second region below the pressure in said first region, mass spectrometric separating apparatus, ion detector apparatus, exit lens structure between said separating apparatus and said detector apparatus, said exit lens structure having an entrance port, an exit port of less than half the diameter of said entrance port, passage structure connecting said entrance and exit ports, said passage structure being smoothly tapered for reducing background noise due to unwanted neutrals and photons, valve structure disposed between said induction coupled plasma apparatus and said second region, operator apparatus coupled to said valve structure for maintaining said valve structure in open position when said analysis system is operating in mass spectrometer mode and for maintaining said valve structure in closed position when said system is operating only optical analysis apparatus mode.

15. A mass spectrometer comprising ion source structure for generating ions of a sample material to be analyzed, structures defining first and second regions adapted to be evacuated, sampling structure adjacent said ion source structure having an orifice through which at least some ions characteristic of said sample material may pass into said first region, focusing apparatus disposed in said first region, mass spectrometric separating apparatus disposed in said second region, ion detector apparatus coupled to said separating apparatus, differential pumping structure between said first and second region said differential pumping structure having a tubular passage and said passage extending into said second region with an exit port in overlapping relation to said separating apparatus, and exit lens structure between said separating apparatus and said detector apparatus, said exit lens structure having an entrance port of at least one centimeter diameter, an exit port of less than half the diameter of said entrance port, and passage structure connecting said entrance and exit ports, said passage structure having a length of at least five millimeters and being smoothly tapered for reducing background noise due to unwanted neutrals and photons.

16. The mass spectrometer of claim 15 wherein said focusing apparatus includes an electrostatic focusing lens system that has a lens axis and plurality of ion lens members, the leading ion lens member being of conical configuration, and circuitry for applying a voltage in the range of −750 to −1500 volts to said leading ion lens member.

17. The mass spectrometer of claim 15 wherein said mass spectrometer has an entrance axis and further including sample cone structure, skimmer cone structure, collection lens cone structure and ion lens cone structure, each said cone structure having an orifice and said orifices being disposed on said entrance axis.

18. A mass spectrometer comprising ion source structure for generating ions of a sample material to be analyzed, structures defining first and second regions adapted to be evacuated, sampling structure adjacent said ion source structure having an orifice through which at least some ions characteristic of said sample material may pass into said first region, focusing apparatus disposed in said first region, mass spectrometric separating apparatus disposed in said second region, ion detector apparatus coupled to said separating apparatus, and exit lens structure between said separating apparatus and said detector apparatus, said exit lens structure having an entrance port, an exit port of less than half the diameter of said entrance port, and passage structure connecting said entrance and exit ports, said passage structure being smoothly tapered for reducing background noise due to unwanted neutrals and photons.

19. An analysis system comprising induction coupled plasma apparatus for generating ions of a sample material to be analyzed, structures defining first and second regions adapted to be evacuated, optical analysis apparatus optically coupled to said induction coupled plasma apparatus for analyzing said sample material, a mass spectrometer for analyzing said sample materials said mass spectrometer having an entrance axis, sampler cone structure skimmer cone structure, collection lens cone structure and ion lens cone structure, each said cone structure having an orifice and said orifices being disposed on said entrance axis, focusing apparatus disposed in said first region, mass spectrometric separating apparatus disposed in said second region, and ion detector apparatus coupled to said separating apparatus valve structure disposed between said collection lens and ion lens cone structures, and operator structure coupled to said valve structure for moving said valve structure between a closed position obstructing said entrance axis and an open position.

20. The system of claim 19 wherein said optical analysis apparatus includes a dispersion grating for dispersing radiation from said plasma apparatus and a solid state detector with a two dimensional detector pixel array optically coupled to said dispersion grating.

21. The system of claim 20 and further including diluter apparatus and controller structure for operating said diluter apparatus to dilute the sample material introduced into said induction coupled plasma apparatus to a solids content of less than 0.2 percent.

22. The system of claim 21 and further including differential pumping structure between said first and second regions, said differential pumping structure having a tubular passage and said passage extending into said second region with an exit port in overlapping relation to said separating apparatus.

23. The system of claim 22 wherein said separating apparatus includes a plurality of mass separating rods and said exit port of said differential pumping structure is disposed within the entrance ends of said mass separating rods.

24. An analysis system comprising induction coupled plasma apparatus for generating ions of a sample material to be analyzed, optical analysis apparatus optically coupled to said induction coupled plasma apparatus for analyzing said sample material, said optical analysis apparatus includes a dispersion grating for dispersing radiation from said plasma apparatus and a solid state detector with a two dimensional detector pixel array optically coupled to said dispersion grating, a mass spectrometer for analyzing said sample material, said mass spectrometer having structures defining first and second regions adapted to be evacuated, an entrance axis, sampler cone structure, skimmer cone structure, collection lens cone structure and ion lens cone structure, each said cone structure having an orifice and said orifices being disposed on said entrance axis, valve structure disposed between said collection lens and ion lens cone structures, operator structure coupled to said valve structure for moving said valve structure between a closed position obstructing said entrance axis and an open position, structure for flowing an inert gas outwardly from said first region through said orifices towards said induction coupled plasma apparatus when said valve structure is closed, focusing apparatus disposed in said first region, spectrometric separating apparatus disposed in said second region, ion detector apparatus coupled to said separating apparatus, diluter apparatus and controller structure for operating said diluter apparatus to dilute the sample material introduced into said induction coupled plasma apparatus to a solids content of less than 0.2 percent, differential pumping structure located between said first and second regions, said differential pumping structure having a tubular passage and said passage extending into said second region with an exit port in overlapping relation to said separating apparatus, said separating apparatus includes a plurality of mass separating rods, and said exit port of said differential pumping structure is disposed within the entrance ends of said mass separating rods.

25. An analysis system comprising induction coupled plasma apparatus for generating ions of a sample material to be analyzed, optical analysis apparatus optically coupled to said induction coupled plasma apparatus for analyzing said sample material, said optical analysis apparatus includes a dispersion grating for dispersing radiation from said plasma apparatus and a solid state detector with a two dimensional detector pixel array optically coupled to said dispersion grating, a mass spectrometer for analyzing said sample material, said mass spectrometer having structures defining first and second regions adapted to be evacuated, an entrance axis, sampler cone structure, skimmer cone structure, collection lens cone structure and ion lens cone structure, each said cone structure having an orifice and said orifices being disposed on said entrance axis, valve structure disposed between said collection lens and ion lens cone structure, operator structure coupled to said value structure for moving said value structure between a closed position obstructing said entrance axis and an open position, focusing apparatus disposed in said first region, mass spectrometric separating apparatus disposed in said second region, ion detector apparatus coupled to said separating apparatus, diluter apparatus and controller structure for operating said diluter apparatus to dilute the sample material introduced into said induction coupled plasma apparatus to a solids content of less than 0.2 percent, differential pumping structure located between said first and second regions, said differential pumping structure having a tubular passage and said passage extending into said second region with an exit port in overlapping relation to said separating apparatus, said separating apparatus includes a plurality of mass separating rods, and said exit port of said differential pumping structure is disposed within the entrance ends of said mass separating rods and exit lens structure between said separating apparatus and said detector apparatus, said exit lens structure having an entrance port of at least one centimeter diameter, an exit port of less than half the diameter of said entrance port, and passage structure connecting said entrance and exit ports, said passage structure having a length of at least five millimeters and being smoothly tapered for reducing background noise due to unwanted neutrals and photons.

26. The system of claim 25 wherein said valve structure includes a gate valve member and further including circuitry for applying voltage in the range of about −750 to −1,500 volts to said collection lens cone structure.

27. An analysis process comprising the steps of providing induction coupled plasma apparatus, optical analysis apparatus optically coupled to said induction coupled plasma apparatus for analyzing sample material, mass spectrometer apparatus coupled to said induction coupled plasma apparatus for analyzing sample material, diluter apparatus and controller structure introducing sample material to be analyzed into said induction coupled plasma apparatus, operating said diluter apparatus to dilute the sample material introduced into said induction coupled plasma apparatus to a solids content of less than 0.2 percent; and sensing outputs from said induction coupled plasma apparatus with said optical analysis apparatus and said mass spectrometer apparatus to analyze said sample material.

28. The process of claim 27 wherein said mass spectrometer apparatus includes structure defining a first region, a sampling member adjacent said induction coupled plasma apparatus that has an orifice through which at least some ions characteristic of said sample material may pass into said first region, structure defining a second region, pump structure coupled to said second region for reducing the pressure in said second region below the pressure in said first region, valve structure disposed between said induction coupled plasma apparatus and said second region, and further including the steps of maintaining said valve structure in open position when said analysis process is operating in mass spectrometer mode and maintaining said valve structure in closed position when said process is operating only in optical analysis mode.

29. An analysis process comprising the steps of providing induction coupled plasma apparatus, optical analysis apparatus optically coupled to said induction coupled plasma apparatus for analyzing said sample material, mass spectrometer apparatus coupled to said induction coupled plasma apparatus for analyzing sample material, said mass spectrometer apparatus includes structure defining a first region, a sampling member adjacent said induction coupled plasma apparatus that has an orifice through which at least some ions characteristic of said sample material may pass into said first region, structure defining a second region, pump structure coupled to said second region for reducing the pressure in said second region below the pressure in said first region, valve structure disposed between said induction coupled plasma apparatus and said second region, diluter apparatus and controller structure introducing sample material to be analyzed into said induction coupled plasma apparatus, operating said diluter apparatus to dilute the sample material introduced into said induction coupled plasma apparatus to a solids content of less than 0.2 percent, maintaining said valve structure in open position when said analysis process is operating in mass spectrometer mode, maintaining said valve structure in closed position when said process is operating only in optical analysis mode, flowing an inert gas from said first region outwardly through said orifice towards said induction coupled plasma apparatus when said valve structure is in closed position, and sensing outputs from said induction couple plasma apparatus with said optical analysis apparatus and said mass spectrometer apparatus to analyze said sample material.

* * * * *

UNITED STATES PATENT AND TRADEMARK OFFICE
CERTIFICATE OF CORRECTION

PATENT NO. : 5,495,107

DATED : February 27, 1996

INVENTOR(S) : Ke Hu et al.

It is certified that error appears in the above-identified patent and that said Letters Patent is hereby corrected as shown below:

On title page, item [56]

In the References Cited section, after "(List continued on next page.), *"American Society For Mass Spectrometry,* 1993, pp. 28-37."* should be moved to page 2 the end of the last "Hu" reference.

Col. 3, line 2, "De" should be --be--;
        line 2, after "embodiments" insert a comma.
        line 21, "or" should be --of--;
        line 24, after "apparatus" insert a comma
        line 30, "Induction" should be --induction--;
        line 43, delete "on".

Col. 4, line 24, after "14," insert --18--;
        line 25, after "diluter" insert --10--.

Col. 8, line 8, after "region" insert a comma.

Col. 9, claim 15, line 48, "region" should be --regions,--.

Col. 10, claim 19, line 26, "materials" should be --material,--;
        line 27, after "structure" insert a comma.

Col. 11, claim 24, line 17, after "region," insert --mass--.

UNITED STATES PATENT AND TRADEMARK OFFICE
CERTIFICATE OF CORRECTION

PATENT NO. : 5,495,107

DATED : February 27, 1996

INVENTOR(S) : Ke Hu et al.

It is certified that error appears in the above-indentified patent and that said Letters Patent is hereby corrected as shown below:

Col. 12, claim 29, line 53, delete "said".

Signed and Sealed this

Twenty-fifth Day of June, 1996

Attest:

Attesting Officer

BRUCE LEHMAN

Commissioner of Patents and Trademarks